(12) United States Patent
Murthy et al.

(10) Patent No.: US 7,439,268 B2
(45) Date of Patent: Oct. 21, 2008

(54) COMPOSITIONS CONTAINING PRODRUGS OF FLORFENICOL AND METHODS OF USE

(75) Inventors: Yerramilli V. S. N. Murthy, Apex, NC (US); Robert H. Suva, Windham, ME (US)

(73) Assignee: Idexx Laboratories, Westbrook, ME (US)

( * ) Notice: Subject to any disclaimer, the term of this patent is extended or adjusted under 35 U.S.C. 154(b) by 662 days.

(21) Appl. No.: 10/623,114

(22) Filed: Jul. 18, 2003

(65) Prior Publication Data

US 2005/0014828 A1      Jan. 20, 2005

(51) Int. Cl.
*A61K 31/205*   (2006.01)
*A61K 31/53*    (2006.01)
*A61K 31/50*    (2006.01)
*A61K 31/505*   (2006.01)
*A61K 31/44*    (2006.01)

(52) U.S. Cl. ............ 514/554; 514/242; 514/247; 514/256; 514/275; 514/352

(58) Field of Classification Search .......... 514/242, 514/247, 256, 275, 352, 554
See application file for complete search history.

(56) References Cited

U.S. PATENT DOCUMENTS

| | | | |
|---|---|---|---|
| 4,235,892 A | 11/1980 | Nagabhushan | |
| 4,311,857 A | 1/1982 | Nagabhushan | |
| 4,361,557 A | 11/1982 | Nagabhushan | |
| 4,382,892 A | 5/1983 | Hayakawa et al. | |
| 4,872,411 A * | 10/1989 | Nagy | 111/7.1 |
| 4,876,352 A | 10/1989 | Schumacher et al. | |
| 5,082,863 A | 1/1992 | Apelian et al. | |
| 5,158,948 A * | 10/1992 | Schoenleber et al. | 514/212.02 |
| 5,336,664 A * | 8/1994 | Camaggi et al. | 504/261 |
| 5,352,832 A | 10/1994 | Wu et al. | |
| 5,382,673 A | 1/1995 | Clark et al. | |
| 5,663,361 A | 9/1997 | Towson et al. | |
| 5,723,447 A | 3/1998 | Macy et al. | |
| 5,756,506 A | 5/1998 | Copeland et al. | |
| 5,866,549 A | 2/1999 | Or et al. | |
| 5,958,888 A | 9/1999 | Macy et al. | |
| 5,977,133 A | 11/1999 | Fung et al. | |
| 6,239,112 B1 | 5/2001 | Macy et al. | |
| 6,660,278 B1 | 12/2003 | Larsson et al. | |
| 6,710,068 B2 * | 3/2004 | LaColla et al. | 514/414 |
| 2002/0065198 A1 * | 5/2002 | Highsmith et al. | 504/206 |
| 2004/0082553 A1 | 4/2004 | Boojamra et al. | |
| 2004/0198704 A1 * | 10/2004 | Shuster et al. | 514/151 |

FOREIGN PATENT DOCUMENTS

WO    WO 0241899    1/1988

OTHER PUBLICATIONS

Bundgaard. Design of prodrugs, pp. 7-9, 21-24, Elseiver, Amsterdam, 1985.*
A. D. Tuddle et al., "Bone Marrow Hypoplasia Secondary to Florfenicol Toxicity in a Thomson's Gazelle" (*Gazella thomsonii*), Journal of Veterinary Pharmacology and Therapeutics, vol. 29, pp. 317-319 (Aug. 2006).
R.H.C. Penny et al., "Effects of Chloramphenicol on the Haemopoietic System of the Cat," British Veterinary Journal, vol. 123, pp. 145-153 (1967).
A.D.J. Watson, "Further Observations on Chloramphenicol Toxicosis in Cats," American Journal of Veterinary Research, vol. 41, pp. 293-294 (Feb. 1980).

* cited by examiner

*Primary Examiner*—Jennifer Kim
(74) *Attorney, Agent, or Firm*—Townsend & Townsend & Crew

(57) ABSTRACT

The present invention provides compositions and methods for administering florfenicol to mammals. The compositions contain a prodrug of florfenicol in a pharmaceutically acceptable carrier. In one embodiment the prodrug is an esterized form of florfenicol. Examples of suitable prodrugs include one or a combination of one or a combination of the following: florfenicol acetate, florfenicol propionate, florfenicol butyrate, florfenicol pentanoate, florfenicol hexanoate, florfenicol heptanoate, florfenicol octanoate, florfenicol nanoate, florfenicol decanoate, florfenicol undecanoate, florfenicol dodecanoate, and florfenicol phthalate. In another embodiment the prodrug is converted into the florfenicol in vivo by the action of one or more endogenous esterases. The invention also provides new compounds, pharmaceutical compositions containing the compounds, and methods for their administration.

19 Claims, 11 Drawing Sheets

R = CH₃ = acetate
 = CH₃ - (CH₂)₂ = butyrate
 = CH₃ - (CH₂)₄ = hexanoate

FLORFENICOL

FLORFENICOL ACETATE

FLORFENICOL BUTYRATE

FLORFENICOL HEXANOATE

FLORFENICOL PHTHALATE

FLORFENICOL SUCCINATE

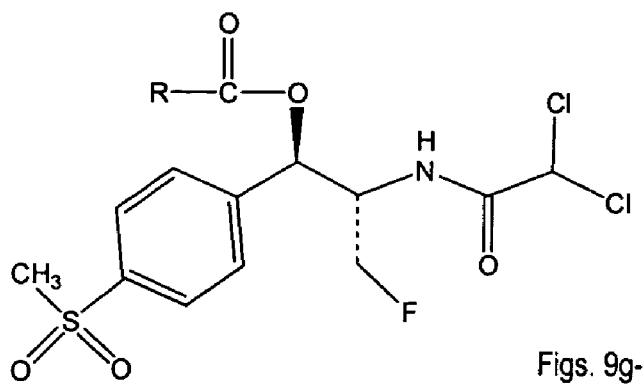
Figs. 9g-n FLORFENICOL DERIVATIVES
Florfenicol Propionate: R= $CH_3CH_2-$
Florfenicol Pentanoate: R= $CH_3(CH_2)_3-$
Florfenicol Heptanoate: R= $CH_3(CH_2)_5-$
Florfenicol Octanoate: R= $CH_3(CH_2)_6-$
Florfenicol Nanoate: R= $CH_3(CH_2)_7-$
Florfenicol Decanoate: R= $CH_3(CH_2)_8-$
Florfenicol Undecanoate: R= $CH_3(CH_2)_9-$
Florfenicol Dodecanoate: R= $CH_3(CH_2)_{10}-$

COMPOSITIONS CONTAINING PRODRUGS OF FLORFENICOL AND METHODS OF USE

FIELD OF THE INVENTION

The present invention pertains to prodrugs for use in mammals.

BACKGROUND OF THE INVENTION

The following discussion of the background of the invention is merely provided to aid the reader in understanding the invention and is not admitted to describe or constitute prior art to the present invention.

Florfenicol is a structural analog of chloramphenicol and thiamphenicol, having a fluorine atom instead of the hydroxyl group located at C-3 in the structure of chloramphenicol and thiamphenicol. Bacterial resistance to chloraniphenicol and thiamphenicol is usually attributed to acetylation of the 3' hydroxyl group by the action of chloramphenicol acetyl transferase. Since florfenicol does not possess the 3' hydroxyl group such a mechanism of inactivation is not possible with florfenicol, thus making florfenicol a highly useful antibiotic.

Florfenicol is active against a variety of microorganisms including *Citrobacter, Proteus mirabilis, Proteus* sp., *Shigella, Salmonella, Providencia, Bacteroides, Staphylococcos aureus, Enterococci, Pasteurlla haemolytica, Pasteurella multocida, Haemophilus somnus,* and *Haemophilus influenza.* Conversely, *Serratia marcescens, Pseudomonas aeruginosa,* and *Acinetobacter,* have been found to be resistant to florfenicol. Literature suggests that typical MICs (minimum inhibitory concentrations) of florfenicol for various bacteria range from 0.3- 1 µg/ml.

Dosage schedules of antibiotics are designed to maintain serum or tissue levels above the MIC for the target organisms for a period of time sufficient to clear the infection. Drugs that are cleared rapidly must be administered more often to maintain effective levels. In the case of some highly hydrophilic drugs, the drugs are cleared from the system so rapidly that their use requires multiple daily doses. Therefore, there is a need for increasing the effectiveness of known hydrophilic antibacterial compounds, such as florfenicol.

SUMMARY OF THE INVENTION

In one aspect, the present invention provides compositions containing a prodrug of florfenicol and a pharmaceutically acceptable carrier in an injectable composition. In one embodiment the prodrug of florfenicol is present in the composition at a concentration of at least 200 mg/ml, while in another embodiment the prodrug of florfenicol is present in the composition at a concentration of about 300 mg/ml. In still another embodiment the prodrug is an esterized form of florfenicol. In various embodiments the prodrug is one or a combination of the following: florfenicol acetate, florfenicol propionate, florfenicol butyrate, florfenicol pentanoate, florfenicol hexanoate, florfenicol heptanoate, florfenicol octanoate, florfenicol nanoate, florfenicol decanoate, florfenicol undecanoate, florfenicol dodecanoate, and florfenicol phthalate. In one embodiment the prodrug is converted into the florfenicol in vivo by the action of an esterase.

By "prodrug" is meant a chemical derivative compound that is transformed in vitro to yield florfenicol through the action of one or more mammalian enzymes. In one embodiment the mammalian enzyme is an esterase. In various embodiments prodrugs are derivatized through an ester linkage between a hydroxyl group of the drug molecule and the carboxyl group of an external acid, or vice versa, to form an esterized form of florfenicol. The term "prodrug ester group" refers to any of many ester-forming groups that are hydrolyzed in the mammalian body. Examples of prodrug ester groups and external acids include acetyl, propionyl, butyryl, pentanyl, hexanyl, heptanyl, octanyl, nonyl, decanyl, undecanyl, dodecanyl, and phthalyl. Other examples of suitable prodrug ester groups and external acids can be found in the book "Pro-drugs as Novel Delivery Systems," by Higuchi and Stella, Vol. 14 of the American Chemical Society Symposium Series, American Chemical Society (1975).

By a "pharmaceutically acceptable carrier" is meant a non-toxic, inert, solid, semi-solid, or liquid filler, diluent, encapsulating material, or formulation auxiliary of any type. In one embodiment the pharmaceutically acceptable carrier is propylene glycol. But many other carriers are available. Examples of pharmaceutically acceptable carriers include, but are not limited to, pyrrolidone, N-methyl pyrrolidone, polyethylene glycol, propylene glycol, glycerol formal, isosorbid dimethyl ether, ethanol, dimethyl sulfoxide, tetrahydrofurfuryl alcohol, triacetin, or any combination of these, or another solvent found to have similar acceptable properties such as being non-toxic and soluble in water. In one embodiment the carrier is propylene glycol in glycerol formal (e.g., in 10% glycerol formal). Other pharmaceutically acceptable carriers include sugars such as lactose, glucose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, arachis oil, sesame oil, olive oil, corn oil, soybean oil, and saw flower oil, ; glycols, such as propylene glycol; polyols such as glycerin, sorbitol, mannitol and polyethylene glycol; esters such as ethyl oleate, isopropyl myristate, and ethyl laurate; agar; ethyl alcohol; as well as other non-toxic compatible substances used in pharmaceutical formulations. Any of these or mixtures thereof can be prepared in a liquid form or dissolved in a suitable liquid to form the carrier. Still other pharmaceutically acceptable carriers include water insoluble or water immiscible solvents. Examples of these include, but are not limited to, isopropyl myristate, and ethyl lactate.

By "injectable" is meant a composition or formulation that is suitable for placing into a syringe and injecting into the mammalian body. The composition and vehicle are tissue-compatible and should not rely on constituents that are likely to elicit an allergic response. Injectable compositions can be injected into the mammalian body without causing adverse effects due to the presence of solid materials in the composition. Solid materials include, but are not limited to, particles, crystals, a gummy mass, and a gel. The injectable compositions can be injected intramuscularly, intra-venously, subcutaneously, intra-dermally, intra-peritoneally, or parenterally, or other suitable modes of injection into the mammalian body.

One injectable composition of the invention contains one or more compounds of the present invention dissolved in glycerol formal with 10% propylene glycol. In one embodiment the composition contains a suspension or solution of one or more compounds of the present invention dissolved in an oil, for example arachis oil or sesame oil. The compositions can also contain one or more compounds of the present invention dissolved in a solvent such as pyrrolidone, N-methyl pyrrolidone, polyethylene glycol, propylene glycol, glycerol formal, isosorbid dimethyl ether, ethanol, dimethyl sulfoxide, tetrahydrofurfuryl alcohol, triacetin, or any combination of these, or another solvent found to have similar acceptable properties such as being non-toxic and soluble in water. The compositions can optionally contain a chelating agent, for example ethylenediamine tetracetic acid and an anti-oxidant, for example sodium metabisulphite.

In another aspect the present invention provides novel compounds. The compounds are one or more compounds having a structure selected from the following: florfenicol acetate, florfenicol propionate, florfenicol butyrate, florfenicol pentanoate, florfenicol hexanoate, florfenicol heptanoate, florfenicol octanoate, florfenicol nanoate, florfenicol decanoate, florfenicol undecanoate, florfenicol dodecanoate, and florfenicol phthalate.

In another aspect the present invention provides pharmaceutical compositions for administration to a mammal. The pharmaceutical compositions contain one or more compounds described herein and a pharmaceutically acceptable carrier, which can be supplied in an injectable form.

In another aspect the present invention provides methods of administering florfenicol to a mammal. The methods involve administering a composition containing a prodrug of florfenicol to the mammal. In one embodiment the composition is administered to the mammal by injection. The composition can form a drug depot in the mammal. The prodrug is converted in vivo by one or more endogenous enzymes into florfenicol. In one embodiment the prodrug is present in the composition at a concentration of at least 250 mg/ml. The prodrug is any of the compound prodrugs described herein, or a combination thereof. In one embodiment the endogenous enzymes are esterases. In various embodiments the mammal is a bovine, an equine, a porcine, an ovine, a canine, or a feline. The compositions can be administered orally, or injected sub-cutaneously, intra-peritoneally, intra-dermally, mucosally, intra-muscularly, or by other means.

A "drug depot" is a reservoir of prodrug situated in the body of the mammal and established by the injection of prodrug through the skin. The drug depot may have a solid, semi-solid, or liquid form, and represents a concentration of prodrug in the treated mammal. In one embodiment the drug depot is a precipitate of the prodrug. The depot then becomes a source of prodrug, and therefore active drug, for the treated mammal. The drug depot can be created and situated in a muscle of the mammal by intra-muscular injection, but can also be situated in other tissue types such as in the dermal layer or in connective tissue. In one embodiment the depot emits prodrug and the prodrug is converted into active drug in the body. In another embodiment the prodrug is converted into active drug at or near the drug depot. In another embodiment the composition in its entirety acts as a drug depot.

By "endogenous enzymes" is meant those enzymes produced or synthesized within the organism by the organism's own protein synthesis apparatus. Endogenous enzymes are those normally found within the organism. They may be produced by the mammalian body continuously or produced in response to a particular stimulus. "Esterase" is a generic term for those enzymes that catalyze the hydrolysis of ester bonds. By "intramuscular" is meant within a muscle. Thus, administration by intramuscular injection means injected into a muscle.

In another aspect the present invention provides methods of administering florfenicol to a mammal. The methods involve injecting into the mammal a composition comprising one or more compounds of the present invention, wherein the one or more compounds is/are converted into florfenicol in vivo by the action of one or more endogenous esterases. In various embodiments the one or more compounds is/are present in the composition at a concentration of at least 250 mg/ml.

The summary of the invention described above is not limiting and other features and advantages of the invention will be apparent from the following detailed description, as well as from the claims.

DETAILED DESCRIPTION OF THE INVENTION

The compositions and methods of the present invention have distinct and surprising advantages over previously available compositions and methods. While the solubilization of florfenicol usually requires relatively strong and harsh solvents, the prodrugs described herein are highly soluble in mild pharmacologically acceptable solvents, such as glycerol formal.

The prodrug compositions of the present invention are efficiently converted to active florfenicol by esterases endogenous in the mammalian system. The butyrate and hexanoate prodrug derivatives are less soluble in water than free florfenicol and display slower release kinetics, while the acetate prodrug derivative is more soluble in water and displays a shorter release time. These chemical characteristics are used to advantage in the present invention. In general the release rate is related to the solubility of the drug in water or biological fluids. When solubility is low, a more viscous depot is formed that releases prodrug more slowly. When solubility is high, the prodrug is released more quickly from the depot resulting in a faster release rate. Florfenicol can be made more hydrophobic by derivatization into various esters. In general, the more hydrophobic the derivative the lower the solubility. Thus, in general the hexanoate derivative is less soluble than the butyrate derivative, which is less soluble than native florfenicol. Thus, when a "fast kill" or "initial burst" of drug is desired, a more soluble prodrug is advantageous to obtain a shorter release time. Longer release times offer the benefit of preventing residual organisms from growing.

Figure 4:
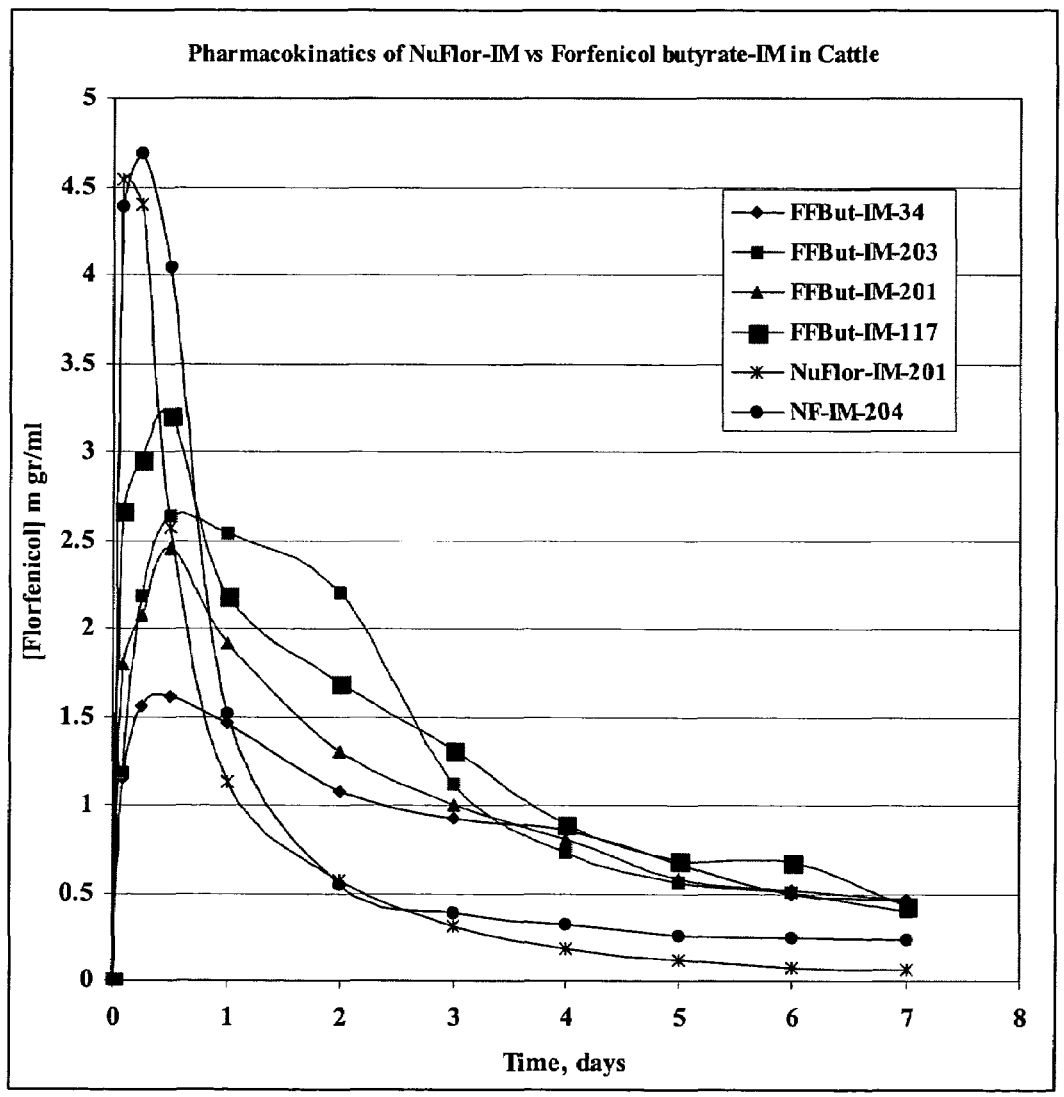
FIG. 4 provides a graphical illustration of the pharmacokinetics of florfenicol and florfenicol ester prodrugs in cattle.

As further described below, a single intra-muscular injection of a florfenicol butyrate prodrug in cattle provided active florfenicol in the serum at higher levels and for longer periods of time than intramuscular injections of NUFLOR® (Schering-Plough Corp., Kenilworth, N.J.), which is a commercially available form of florfenicol. Furthermore, a single subcutaneous injection of the butyrate and hexanoate ester prodrug formulations in cats was found to provide serum florfenicol concentrations above the minimum inhibitory concentration (MIC) for a period of 4-6 days, while serum concentrations of NUFLOR® drop off significantly after 2 days (FIG. 4).

Without being bound by any particular theory, it is believed that after injection the water-soluble pharmaceutically acceptable carrier diffuses away from the injection site, thereby resulting in the formation of a drug depot containing the prodrug. In one embodiment the drug depot is a precipitate of the prodrug. As the pro-drug slowly dissolves and is released from the depot into the serum over time, it is hydrolyzed by endogenous esterases into active florfenicol, thereby providing a continuous source of florfenicol at effective levels. Thus, the difficulties associated with florfenicol are overcome in the present invention by converting the relatively hydrophilic florfenicol molecule into a highly hydrophobic molecule that forms in vivo drug depots providing long release times.

Further information regarding the compositions and methods of the present invention is provided with reference to the following non-limiting examples.

EXAMPLE 1

Ester Formation

Esters can be formed by the reaction of acids with alcohols. The formation of esters can be viewed as the substitution of the OH group on the acid by the alcohol group, and the proton on the alcohol combined with the acid OH to form water.

In one embodiment of the invention, the ester is formed by the reaction of an acid anhydride with an alcohol (florfenicol). Thus, an acid anhydride of the derivative(s) being formed is obtained and reacted under catalytic conditions with florfenicol to form the ester derivative. The catalytic conditions are provided by the presence of a strong acid, such as perchloric or concentrated sulfuric acid. The reaction is rapid, irreversible, and lies far to the right. Yields of nearly 100% are obtainable using little or no excess acid anhydride. The reaction can be depicted as:

In another embodiment florfenicol can be reacted with a carboxylic acid in the presence of a catalyst. This reaction principle is known as "Fischer esterification." Appropriate catalysts include strong acids such as concentrated sulfuric acid, hydrogen chloride, or p-toluenesulfonic acid. This type of reaction is an equilibrium reaction, which must be refluxed for several hours. Higher yields can be obtained by using excessive amounts of acid or alcohol, as the reaction does not lie far to the right.

In a third method, esters can be formed by reacting an acid chloride with florfenicol. The reaction is quantitative and rapid. The acid chloride is the corresponding derivative to be synthesized. This reaction produces hydrogen chloride and pyridine can be added to neutralize this reaction product.

The above three methods of forming esters are provided only as examples. Other methods are known to those of ordinary skill in the art, and more methods may yet be discovered, that can be applied in the present invention. Such other methods are also contemplated for use herein. Since esters can be formed from a wide variety of acids, a very large number of esters is possible. In the methods, combinations of several acids can be combined with florfenicol to form a mixture of several different ester derivatives.

EXAMPLE 2

Preparation of Prodrugs

Figure 1:
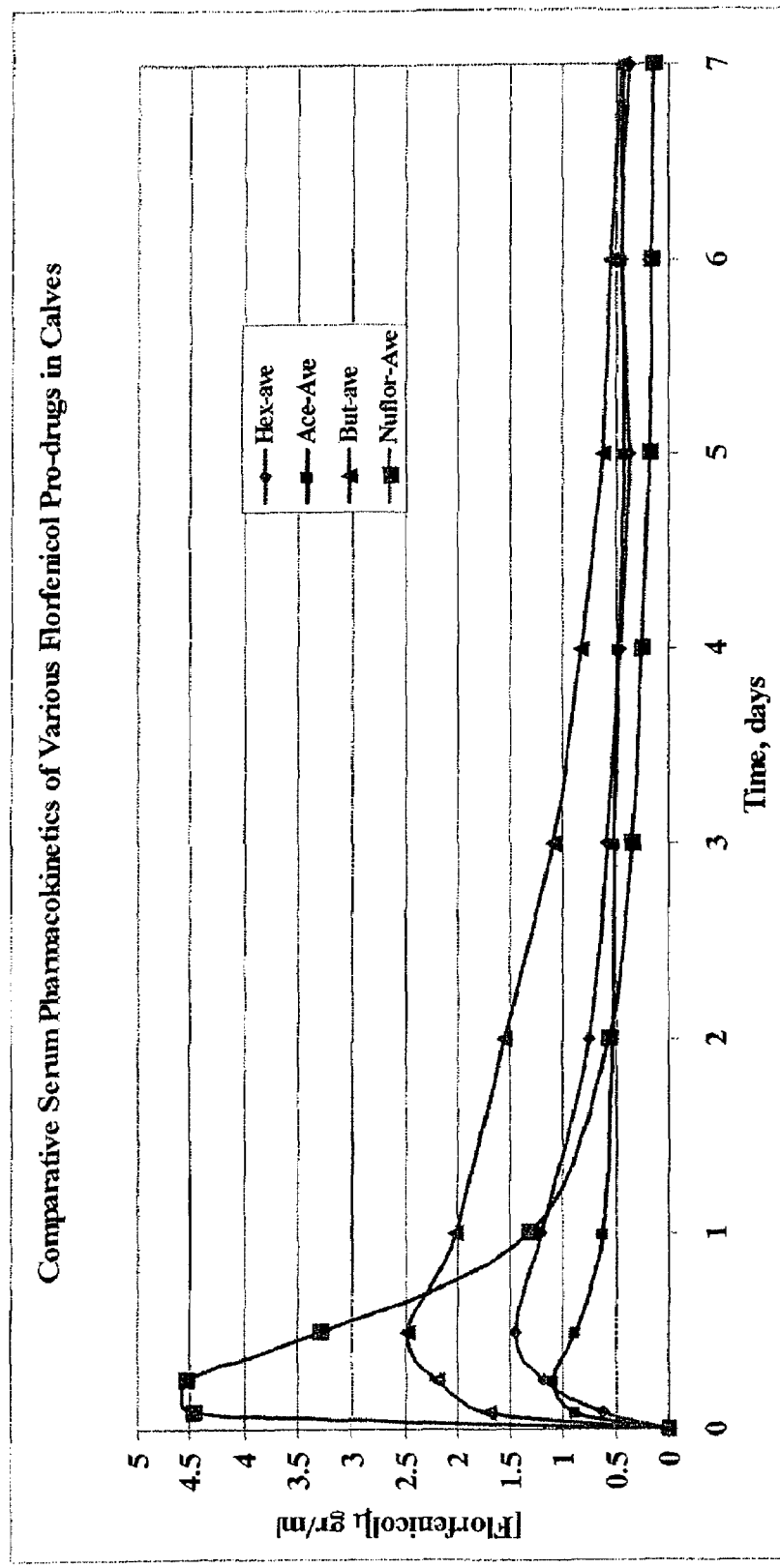
FIG. 1 provides a schematic illustration of the prodrug conversion process.
Figure 2:
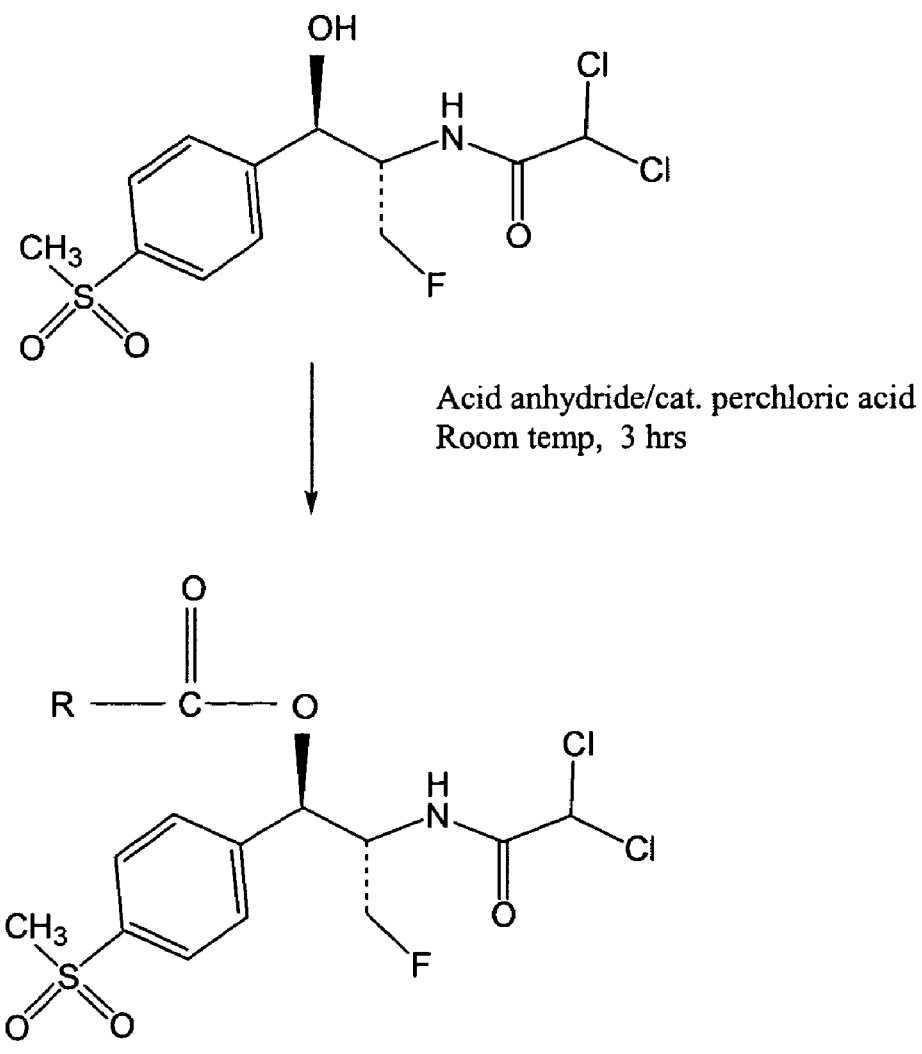
FIG. 2 provides a schematic illustration of the synthesis of florfenicol ester prodrugs.

Florfenicol acetate, florfenicol butyrate, and florfenicol hexanoate ester pro-drugs were synthesized as shown in FIG. 2, using a simple one step synthetic procedure. The procedure utilized was the acid anhydride procedure.

Thus, florfenicol was suspended in the corresponding acid anhydride followed by the addition of a catalytic amount of perchloric acid under conditions suitable for esterization to occur such as, for example, stirring at room temperature for about 3 hours. Generally, this embodiment involves adding solid florfenicol to liquid anhydride. The florfenicol is not soluble in anhydride and stays as a suspension. Once perchloric acid is added, product begins to form and dissolve in the solution. After sufficient time a completely clear solution is obtained and product begins to crystallize out of solution. The following examples are suitable procedures for preparing prodrugs.

Florfenicol butyrate: 225 g of florfenicol was suspended in 330 ml of butyric anhydride in one liter round bottom flask equipped with a over head stirrer and a drying tube. To this suspension was added one ml of perchloric acid, while stirring vigorously, with a pipette. A clear solution was obtained in a few minutes. Stirring was continued for another 3 hours during which the florfenicol butyrate pro-drug was crystallized. The solid product was filtered using a Buckner funnel under vacuum, and washed thoroughly with hexane. The product was finally crystallized in ethanol and the crystallized product was washed with hexane and dried to obtain around 230 g of solid florfenicol butyrate.

Florfenicol acetate: 250 g of florfenicol was suspended in 330 ml of acetic anhydride in one liter round bottom flask equipped with a over-head stirrer and a drying tube. To this suspension was added one ml of perchloric acid, while stirring vigorously with a pipette. A clear yellow solution was obtained in a few minutes. Stirring was continued for another 3 hours. After 3 hrs, the reaction mixture was poured into 1000 g of ice and stirring continued to arrive at a suspension of product. Solid present was filtered and resuspended in 500 ml of water, and then stirred for 10 min to remove residual acetic acid. The solid product was filtered using a Buckner finnel under vacuum and then recrystallized in ethanol. The recrystallized product was washed with hexane and dried to obtain around 260 g of solid florfenicol acetate.

Florfenicol hexanoate: 100 g of florfenicol was suspended in 500 g of hexanoic anhydride in one liter round bottom flask equipped with an overhead stirrer and a drying tube. To this suspension was added 3 ml of perchloric acid, while stirring vigorously, with a pipette. A clear solution was obtained in a few minutes. Stirring was continued for another 3 hours during which the product, florfenicol hexanoate pro-drug was recrystallized. The solid product was filtered using Buckner finnel under vacuum, washed thoroughly with hexane. The product was finally recrystallized in ethanol and the recrystallized product was washed with hexane and dried to obtain around 117 g of solid florfenicol hexanoate.

Florfenicol phthalate: 3.9 g of florfenicol, 3.6 g of phthalic anhydride and 7.2 ml of triethyl amine in 36 ml of dioxane were taken in a 100 ml round bottom flask equipped with a magnetic stir bar and a drying tube. The reaction mixture was stirred at room temperature for 6 hours. After 6 hours, the contents were poured into 300 ml of cold water. The resulting gummy solid was dissolved in dichloromethane and washed thoroughly with saturated bicarbonate several times followed by water. The organic layer was dried over anhydrous sodium sulfate and concentrated over roto-evaporator. The semisolid obtained was recrystallized in a mixture of ethylacetate and hexane to obtain a solid product of 4.2 grams.

EXAMPLE 3

In vitro Release Kinetics

The following example illustrates the preparation of formulations and analysis of the release kinetics for florfenicol acetate, florfenicol butyrate, and florfenicol hexanoate. Other prodrug formulations can be prepared and analyzed using the same principles such as, for example, florfenicol propionate, florfenicol pentanoate, florfenicol heptanoate, florfenicol octanoate, florfenicol nanoate, florfenicol decanoate, florfenicol undecanoate, florfenicol dodecanoate, and florfenicol phthalate. Each prodrug was prepared as an injectable formulation at 300 mg/ml in non-aqueous carriers including propylene glycol, glycerol formal, N-methyl-pyrrolidone (NMP), and polyethylene glycol (PEG).

7.5 grams of florfenicol butyrate, florfenicol hexanoate, and florfenicol acetate were transferred to individual 25 ml volumetric flasks. 2.5 ml of propylene glycol was added to each solid, followed by the addition of glycerol formal to a final volume of 25 ml. The flask was placed on a shaker for about 2 hours to obtain a clear homogeneous solution.

In vitro release kinetics of the prodrug formulations and a solution of florfenicol in NMP were studied using a dialysis technique. A 0.5 ml aliquot of each formulation was injected into a SLIDE-A-LYZER® dialysis cassette (Pierce Biotechnology, Inc., Rockford, Ill.), and each cassette was suspended in a flask containing 150 ml of phosphate-buffered saline, 10 mM phosphate, 120 mM NaCl, pH 7.4.

The ester prodrug was observed to precipitate in the bag within about an hour. The acetate prodrug was found to be more soluble in aqueous carriers, while the butyrate and hexanoate derivatives formed precipitates more readily and were less soluble in aqueous carriers such as the phosphate buffer. Aliquots were removed from the flasks at various intervals and florfenicol esters were determined by HPLC. The in vitro release samples were directly injected after filtering through a 0.2 um filter in phosphate-buffered saline.

Samples were analyzed on a reversed phase C-18 column with detection at 223 nm, using acetonitrile and water as the solvent system. The gradient started at 25% acetonitrile rising to 60% acetonitrile over 10 minutes. From 20-42 minutes the acetonitrile was lowered to 25%. The flow rate was 1.2 ml/min.

Figure 3:
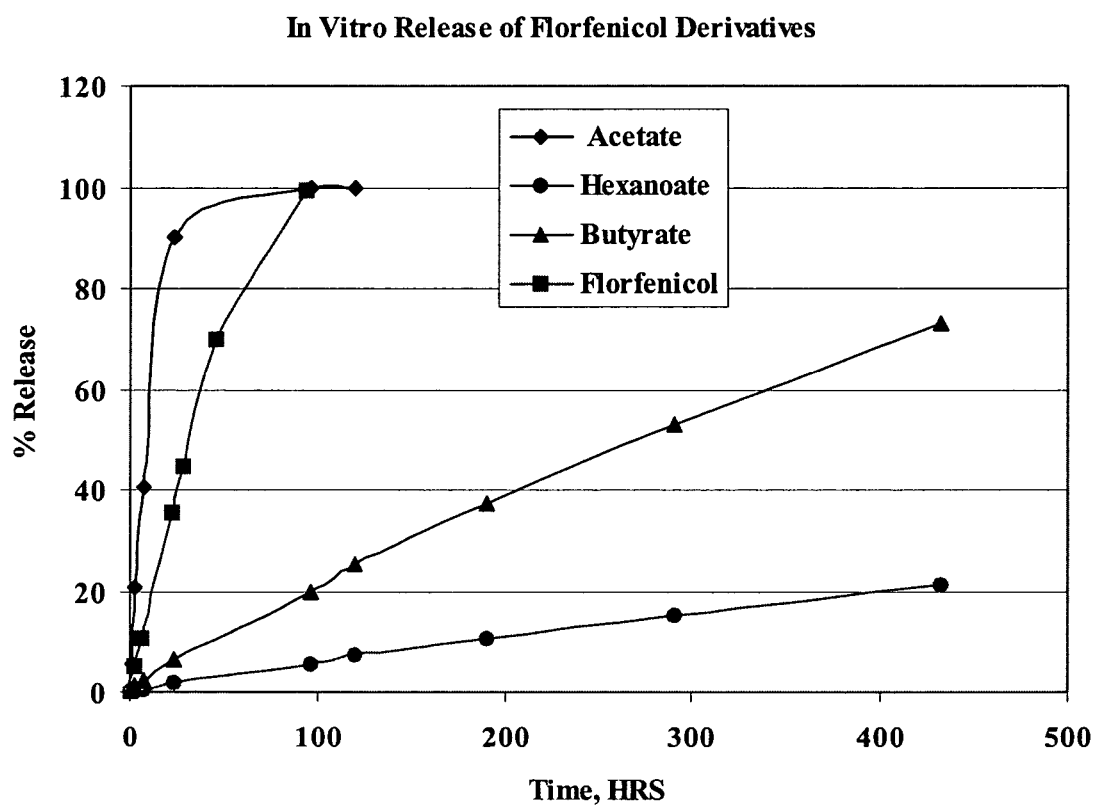
FIG. 3 provides a graphical illustration of the in-vitro release kinetics of florfenicol and florfenicol ester prodrugs.

FIG. 3 illustrates the release kinetics for each florfenicol prodrug. The acetate prodrug was found to display faster release kinetics compared to florfenicol, while the butyrate and hexanoate derivatives displayed slower release kinetics compared to native florfenicol.

EXAMPLE 4

Minimum Inhibitory Concentrations

The Minimum Inhibitory Concentrations (MICs) were determined for each ester derivative in the presence and absence of pig liver esterase (PLE) with florfenicol (NUFLOR®, Schering-Plough, Kenilworth, N.J.) as a control. The results are summarized in Table 1. The results illustrate that the prodrugs have comparable MICs to the native florfenicol in the presence of PLE, while no activity was observed in the absence of the enzyme. Higher MICs were observed with the acetate prodrug than with the butyrate and hexanoate prodrugs, presumably because acetate is a poor substrate for PLE.

TABLE 1

Determination of MICs for Florfenicol Derivatives

| | MIC (ug/ml) | | | | | | | |
|---|---|---|---|---|---|---|---|---|
| | Nuflor® | FFAc | FFBut | FFHex. | Nuflor® w/est. | FFAc w/est. | FFBut w/est. | FFHex. w/est. |
| E. coli 25922 | 6.25 | >200 | >200 | >200 | 6.25 | 200 | 25 | 12.5 |
| Klebsiella pneumoniae 31488 | 1.56 | 200 | >200 | >200 | 1.56 | 100 | 12.5 | 6.25 |
| Pseud. aeruginosa 27853 | 200 | >200 | >200 | >200 | >200 | >200 | >200 | >200 |
| Serratia marcescens 14757 | 25 | >200 | >200 | >200 | 25 | 200 | 100 | 25 |
| Proteus mirabilis 29906 | 6.25 | 200 | >200 | >200 | 6.25 | 200 | 25 | 6.25 |

Dilution series: 200, 100, 50, 25, 12.5, 6.25, 3.125, 1.56

Key
FFAc = Florfenicol acetate
FFBut = Florfenicol butyrate
FFHex = Florfenicol hexanoate
w/est. = with esterase

EXAMPLE 5

Hydrolysis of Prodrug by Esterases

The conversion of florfenicol esters to florfenicol by the esterases present in dog and cat serum and whole blood was studied. Each of the prodrugs to be analyzed was prepared at a concentration of 300 mg/ml solution of the prodrug in 10% propylene glycol in glycerol formal. 0.1 ml aliquots of these preparations were spiked into 1.933 ml of blood and serum and the conversion to active florfenicol at 37° C. was studied. 100 ul aliquots were loaded onto a solid phase extraction (SPE) cartridge and the drug/pro-drug was extracted. The results are summarized in Table 2 and illustrate that all three esters are substrates to both canine and feline esterases.

TABLE 2

Percent Hydrolysis of Florfenicol Esters in
Canine Plasma and Whole Blood After 24 Hrs

|  | Plasma | Whole blood |
|---|---|---|
| Florfenicol | 100 | 100 |
| Florfenicol acetate | 51 | 96 |
| Florfenicol butyrate | 80 | 96 |
| Florfenicol hexanoate | 94 | 88 |

EXAMPLE 6

Animal to Animal Variations

Animal to animal variations in hydrolysis rates were also examined. Florfenicol buyrate was spiked into whole blood from five different dogs and the percent conversion to florfenicol after 30 minutes was determined by HPLC analysis. The results are shown in Table 3 and illustrate that no significant change in the hydrolysis rate was observed within the group of five animals.

TABLE 3

Percent Hydrolysis of Florfenicol Butyrate in
Canine Whole Blood After 30 Minutes

| Dog# | % Hydrolysis |
|---|---|
| 34410 | 83 |
| 35752 | 94 |
| 35803 | 98 |
| 35870 | 90 |
| 35872 | 100 |

EXAMPLE 7

Intra-Muscular Administration to Cattle

This example describes the administration of various florfenicol ester prodrug formulations by injection into cattle with the serum being analyzed for the presence of florfenicol and prodrug.

HPLC analysis of the serum from the injected animals showed a florfenicol peak and no ester derivative peaks. These results illustrate the conversion of prodrug to active florfenicol in vivo.

Florfenicol butyrate was formulated at 350 mg/ml in 10% propylene glycol in glycerol formal as described above and injected intramuscularly into four calves at a dosage of 40 mg/kg calf. Commercially available NUFLOR® was used as a control and was injected as a single dose of 20 mg/kg as per label. Injections were administered to the muscles of the neck or the buttocks. Serum samples from the injected animals were analyzed for florfenicol and the results are summarized in FIG. 4. With NUFLOR®, the serum concentrations built up rapidly to a high of about 4.5 mg/ml, and then declined rapidly. With the florfenicol butyrate the serum concentrations also built up rapidly but decreased more slowly, thus extending the area under curve and retaining active florfenicol in the serum at effective levels for a longer period of time. Thus, during days 2-7 the serum concentrations obtained using florfenicol butyrate were higher compared to those where NUFLOR® was used. These data illustrate that the pro-drug formulation provided for the controlled release of florfenicol, thus keeping therapeutic levels of florfenicol in the serum for a longer period time, while the NUFLORE® formulation resulted in a rapid build up and a rapid decrease.

EXAMPLE 8

Sub-Cutaneous Florfenicol Butyrate in Cats

Figure 5:
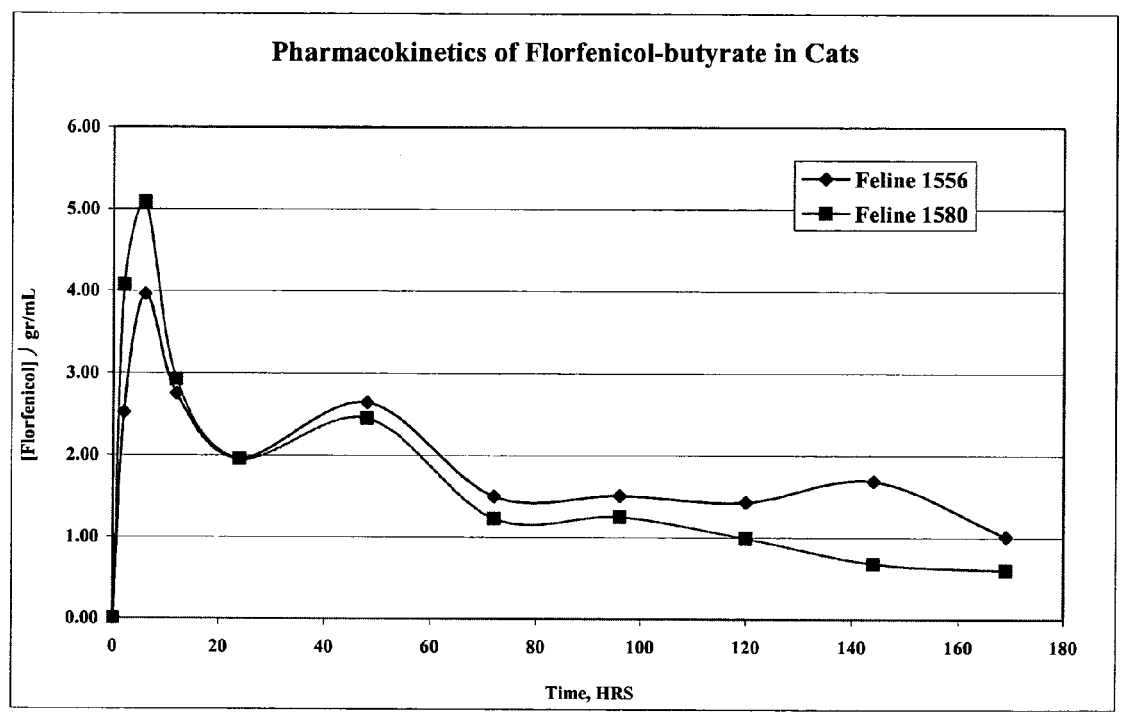
FIG. 5 provides a graphical illustration of the pharmacokinetics of florfenicol butyrate in cats.

Florfenicol butyrate was formulated at 300 mg/ml in 10% propylene glycol in glycerol formal as described above and injected sub cutaneously into two cats at a dose of 40 mg/kg of cat. Both animals showed serum concentrations of florfenicol of greater than 1.0 ug/ml (the MIC) for 5-6 days, with serum concentrations peaking at 4-5 ug/ml. An illustration of the data is provided in FIG. 5.

Figure 8:
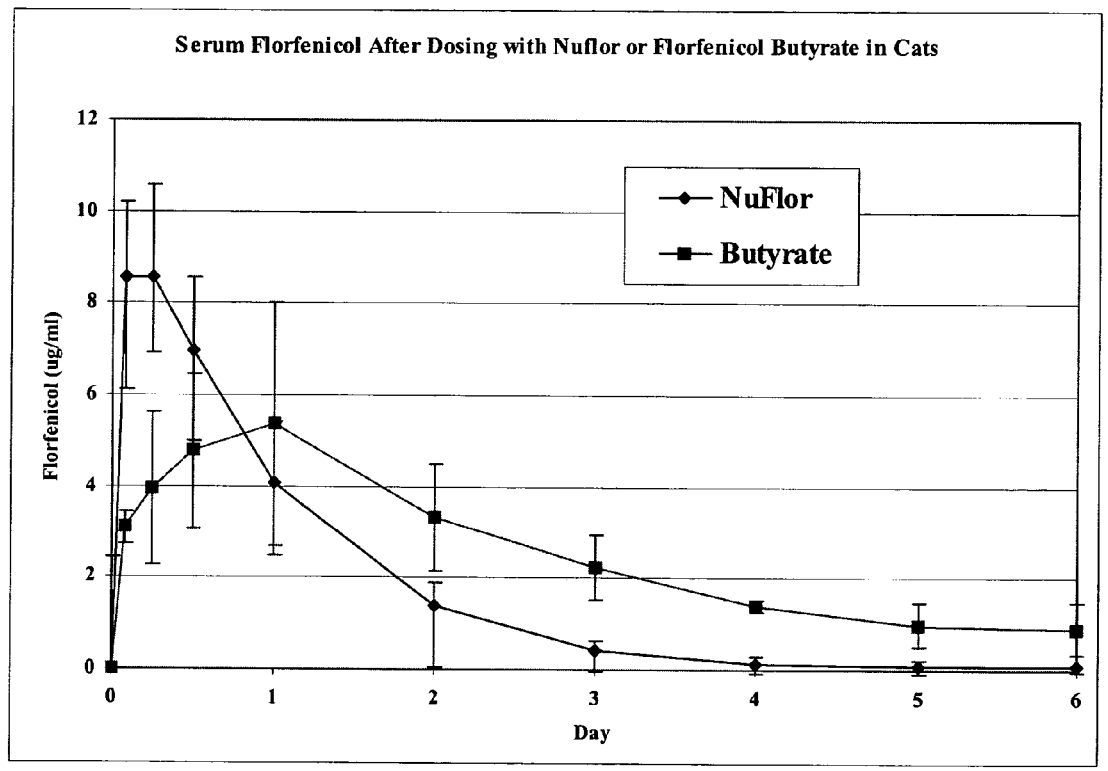
FIG. 8 provides a graphical illustration of serum concentrations of florfenicol butyrate v. NUFLOR® (Schering-Plough Corp., Kenilworth, N.J.) in cats.
Figure 9A:
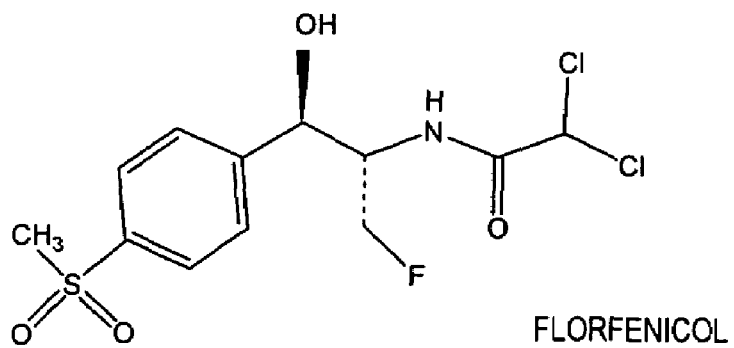
FIGS. 9a-n provide illustrations of examples of compounds of the present invention.
Figure 9B:
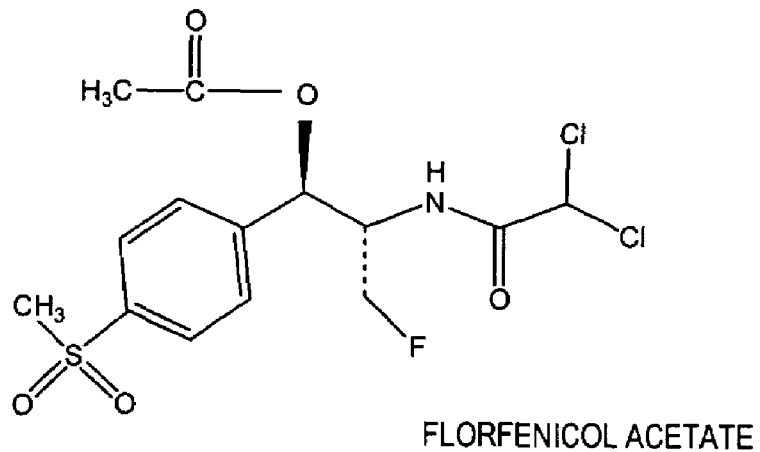
Figure 9C:
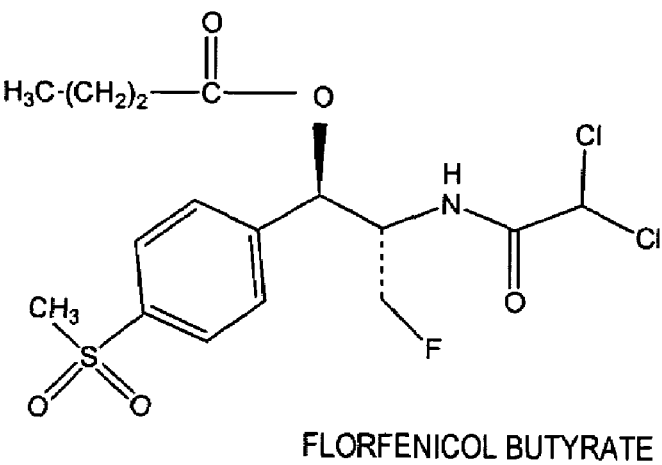
Figure 9D:
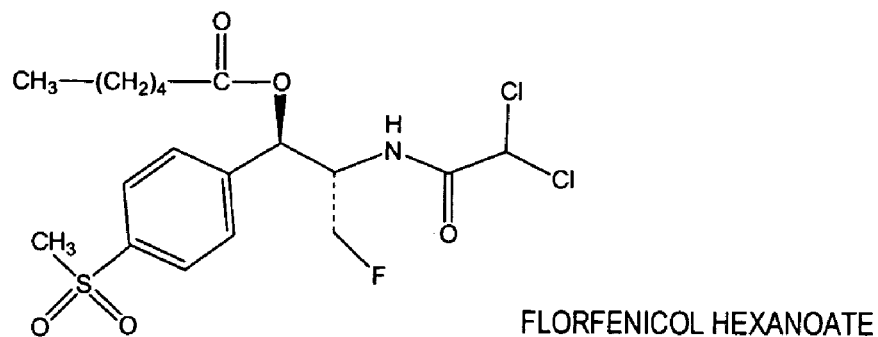
Figure 9E:
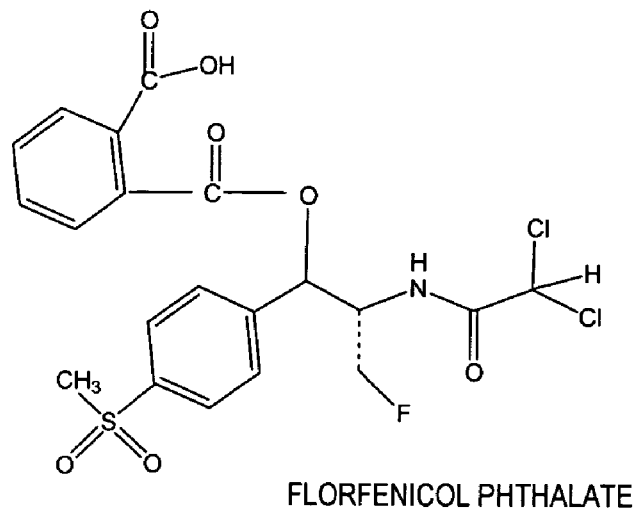
Figure 9F:
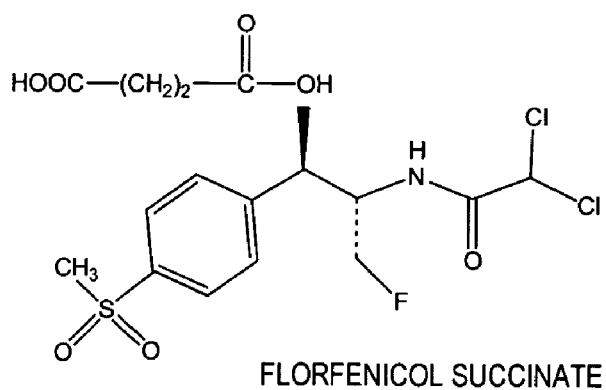

In a separate experiment florfenicol butyrate was formulated at 350 mg/ml in 10% propylene glycol in glycerol formal and injected subcutaneously into five cats at a dosage of 40 mg/kg. Commercially available NUFLOR® was used as a control and was also injected at a dosage of 40 mg/kg. Serum samples from the injected animals were analyzed for the presence of florfenicol, and the results are graphically depicted in FIG. 8. Concentrations of NUFLOR® built up rapidly in the serum and then declined rapidly over two days. Conversely, the concentration of florfenicol butyrate built up less rapidly and declined more slowly than that of NUFLOR®. Thus, the florfenicol butyrate was released more slowly than NUFLOR®. FIG. 8 demonstrates that serum concentrations of florfenicol butyrate are higher compared to NUFLOR® for days 2-6. Therefore, the florfenicol pro-drug formulation provided the controlled release of the active at therapeutic levels for a longer period of time than NUFLOR®.

EXAMPLE 9

Sub-Cutaneous Florfenicol Hexanoate in Cats

Figure 6:
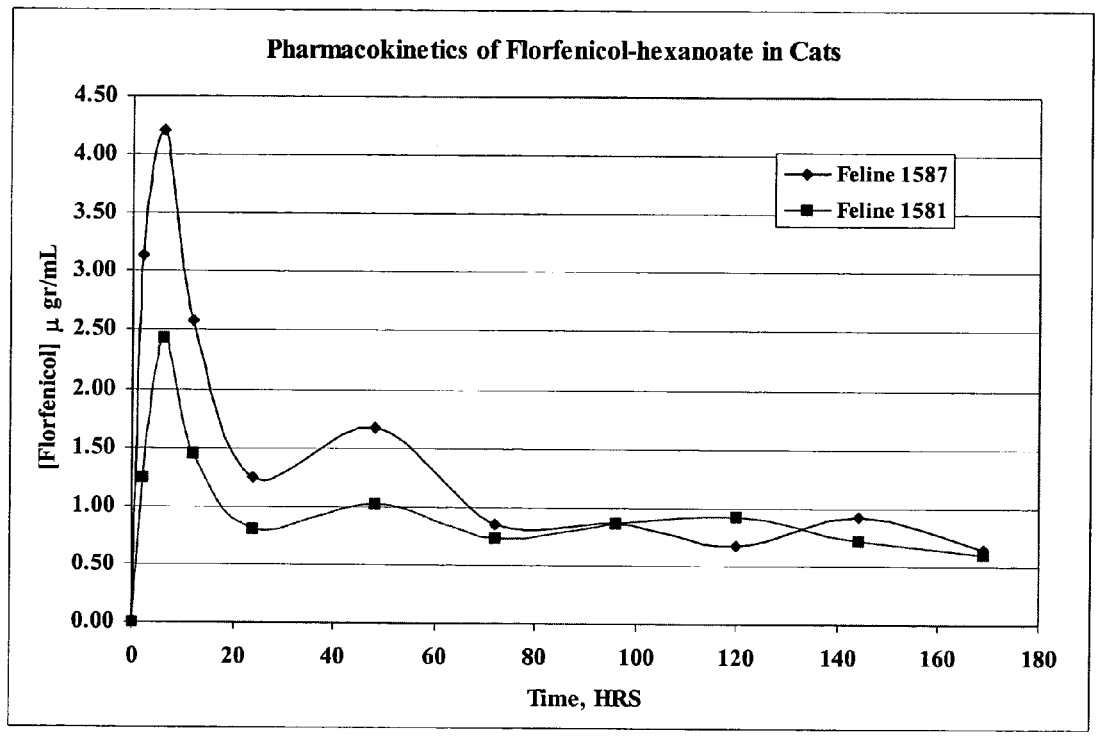
FIG. 6 provides a graphical illustration of the pharmacokinetics of florfenicol hexanoate in cats.

In this example florfenicol hexanoate was formulated at 300 mg/ml in 10% propylene glycol in glycerol formal as described above and injected sub-cutaneously into two cats at a dose of 40 mg/kg of cat. Both animals showed serum florfenicol concentrations above 1.0 ug/ml for 6 days with high concentrations at 2.5-4 ug/ml. The results are illustrated in FIG. 6.

EXAMPLE 10

Mixture of Florfenicol Derivatives Sub-Cutaneous in Cats

Figure 7:
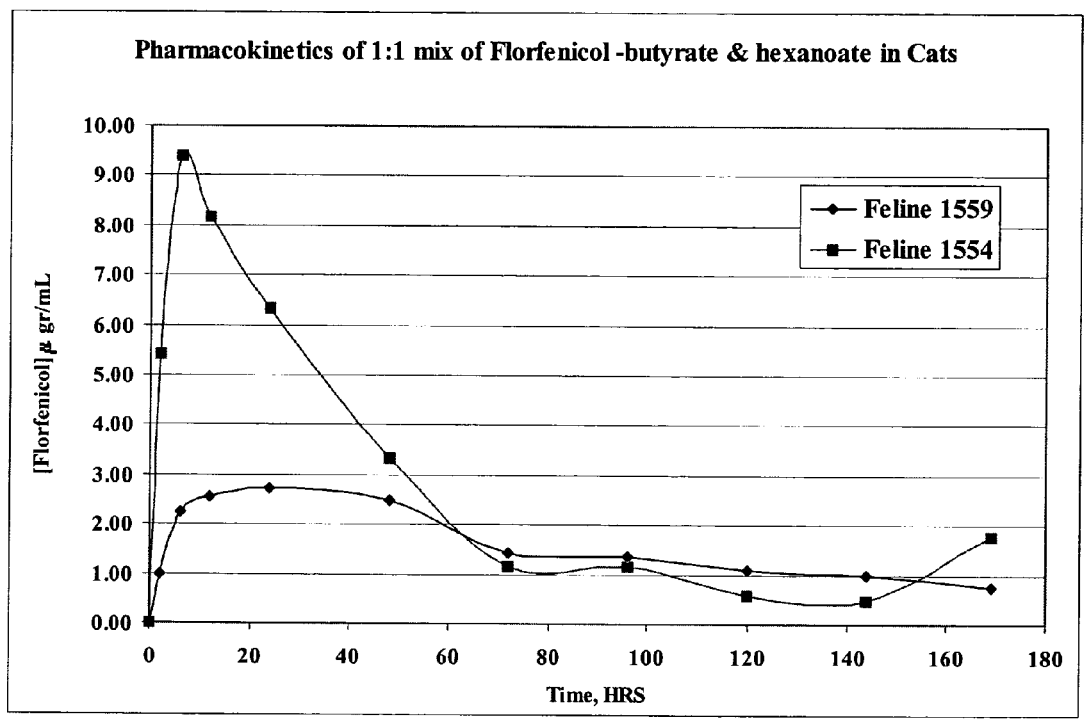
FIG. 7 provides a graphical illustration of the pharmacokinetics of florfenicol butyrate and hexanoate in cats.

In this example a 1:1 ratio mixture of florfenicol butyrate and florfenicol hexanoate was formulated at 300 mg/ml in 10% propylene glycol in glycerol formal as described above and injected sub-cutaneously into two cats at a dose of 40 mg/kg of cat. Both animals showed serum concentrations of florfenicol of greater than 1.0 ug/ml for 4-6 days, with high concentrations of 2.5-10 ug/ml. The results are graphically illustrated in FIG. 7.

EXAMPLE 11

Florfenicol Acetate Sub-Cutaneous in Cats

In this example florfenicol acetate was formulated at 300 mg/ml in 10% propylene glycol in glycerol formal as described above and injected sub-cutaneously into a cat at a dose of 40 mg/kg of cat. Serum samples were analyzed periodically at 0, 1, 6, and 24 hours after the injection. The results are summarized below in Table 4, which indicates the serum concentrations of florfenicol and acetate at the indicated time intervals after injection. A considerably higher concentration of drug was found at 24 hours after injection than found when using the butyrate and hexanoate derivatives. Un-hydrolyzed acetate ester was also noted at a serum concentration of about 5 ug/ml.

Without being bound by any particular theory, it is believed by the inventors that the acetate esters are released more rapidly into the bloodstream than the butyrate and hexanoate esters. However, the hydrolysis rate is less with the acetate ester, which may be caused by it being a poorer substrate for the endogenous esterases.

|  | Time (hrs) | | | |
| --- | --- | --- | --- | --- |
|  | 0 hours | 1 hour | 6 hours | 24 hours |
| [Florfenicol] (ug/ml) | 0 | 4.18 | 15.49 | 3.93 |
| [Acetate] (ug/ml) | 0 | 5.70 | 5.4 | 0.5 |

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The invention claimed is:

1. A composition comprising florfenicol butyrate and a pharmaceutically acceptable solvent selected from N-methyl pyrrolidone, pyrrolidone, polyethylene glycol, propylene glycol, glycerol formal, isosorbid dimethyl ether, ethanol, dimethyl sulfoxide, tetrahydrofurfuryl alcohol, triacetin, and combinations thereof, wherein the composition is formulated as a composition for administration to a mammal by injection.

2. The composition of claim 1, wherein the solvent is selected from propylene glycol, glycerol formal, and combinations thereof.

3. The composition of claim 2, wherein the pharmaceutically acceptable solvent is a combination of propylene glycol and glycerol formal.

4. The composition of claim 1, wherein the concentration of florfenicol butyrate in the composition is at least about 200 mg/mL.

5. A method of treating a bacterial infection in a feline comprising injecting the feline with the pharmaceutical composition of claim 1.

6. A method of treating a bacterial infection in a feline comprising injecting the feline with the pharmaceutical composition of claim 2.

7. A method of treating a bacterial infection in a feline comprising injecting the feline with the pharmaceutical composition of claim 3.

8. A method of treating a bacterial infection in a feline comprising injecting the feline with the pharmaceutical composition of claim 4.

9. The pharmaceutical composition of claim 1, wherein the solvent is selected from the group consisting of propylene glycol, glycerol formal, N-methyl pyrrolidone, and combinations thereof.

10. The pharmaceutical composition of claim 9, wherein the solvent is a combination of propylene glycol, glycerol formal, and N-methyl pyrrolidone.

11. The pharmaceutical composition of claim 9, wherein the solvent is a combination of propylene glycol and N-methyl pyrrolidone.

12. The pharmaceutical composition of claim 9, wherein the solvent is a combination of glycerol formal and N-methyl pyrrolidone.

13. The pharmaceutical composition of claim 1, wherein the solvent is selected from the group consisting of tetrahydrofurfuryl alcohol, N-methyl pyrrolidone, and combinations thereof.

14. The pharmaceutical composition of claim 13, wherein the solvent is a combination of tetrahydrofurfuryl alcohol and N-methyl pyrrolidone.

15. The pharmaceutical composition of claim 1, wherein the solvent is selected from the group consisting of propylene glycol, glycerol formal, N-methyl pyrrolidone, polyethylene glycol, and combinations thereof.

16. The pharmaceutical composition of claim 15, wherein the solvent is a combination of polyethylene glycol and N-methyl pyrrolidone.

17. The pharmaceutical composition of claim 15, wherein the solvent is a combination of polyethylene glycol and glycerol formal.

18. The pharmaceutical composition of claim 15, wherein the solvent is a combination of polyethylene glycol and propylene glycol.

19. The pharmaceutical composition of claim 15, wherein the solvent is a combination of polyethylene glycol, propylene glycol, and N-methyl pyrrolidone.

* * * * *